United States Patent
Flohr et al.

(10) Patent No.: US 7,449,461 B2
(45) Date of Patent: Nov. 11, 2008

(54) BENZATHIAZOL-ACETAMIDES

(75) Inventors: Alexander Flohr, Reinach (CH); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 218 days.

(21) Appl. No.: 11/181,573

(22) Filed: Jul. 14, 2005

(65) Prior Publication Data

US 2006/0019950 A1  Jan. 26, 2006

(30) Foreign Application Priority Data

Jul. 22, 2004 (EP) .................... 04103508

(51) Int. Cl.
*A61K 31/535* (2006.01)
*C07D 415/00* (2006.01)

(52) U.S. Cl. ............... 514/235.5; 514/233.5; 544/133

(58) Field of Classification Search ........... 514/235.5, 514/233.5; 544/133
See application file for complete search history.

(56) References Cited

U.S. PATENT DOCUMENTS

| | | | |
|---|---|---|---|
| 6,284,759 B1 * | 9/2001 | He ....................... | 514/252.19 |
| 6,521,754 B2 * | 2/2003 | Alanine et al. ......... | 544/129 |
| 2003/0153566 A1 | 8/2003 | Flohr et al. | |
| 2004/0235842 A1 | 11/2004 | Flohr et al. | |
| 2004/0242576 A1 | 12/2004 | Flohr et al. | |

FOREIGN PATENT DOCUMENTS

| | | |
|---|---|---|
| WO | WO 01/97786 | 12/2001 |
| WO | WO 03/043634 | 5/2003 |
| WO | WO 03/043636 | 5/2003 |
| WO | WO 03/045386 | 6/2003 |
| WO | WO 03/049741 | 6/2003 |

OTHER PUBLICATIONS

Poulsen, et al., Bioorganic and Medicinal Chemistry 6(6) 619-641, 1998 Adenosine receptors: New opportunities for future drugs.
Müller et al., Bioorganic and Medicinal Chemistry 6(6) 707-719, 1998 8-(Sulfostyryl)xanthines: water-soluble $A_{2A}$-selective adenosine receptor antagonists.
Kim et al., Journal of Medicinal Chemistry 41(15) 2835-2845, 1998 Derivatives of the Triazoloquinazoline Adenosine Antagonist (CGS 15943) Having High Potency at the Human $A_{2B}$ and $A_3$ Receptor Subtypes.
Li et al., Journal of Medicinal Chemistry 41(17) 3186-3201, 1998 Structure-Activity Relationships and Molecular Modeling of 3,5-Diacyl-2,4-dialkylpyridine Derivatives as Selective $A_3$ Adenosine Receptor Antagonists.
Baraldi, et al., Journal of Medicinal Chemistry 41(12) 2126-2133, 1998 Design, Synthesis, and Biological Evaluation of a Second Generation of Pyrazolo[4,3-e]-1,2,4-triazolo[1,5-c]pyrimidines as Potent and Selective $A_{2A}$ Adenosine Receptor Antagonists.
Li et al., Journal of Medicinal Chemistry 42(4) 706-721, 1999 Synthesis, CoMFA Analysis, and Receptor Docking of 3,5-Diacyl-2,4-Dialkylpyridine Derivatives as Selective $A_3$ Adenosine Receptor Antagonists.
Baraldi et al., Journal of Medicinal Chemistry 39(5) 1164-1171, 1996 Pyrazolo[4,3-e]-1,2,4-triazolo[1,5-c]pyrimidine Derivatives: Potent and Selective $A_{2A}$ Adenosine Antagonists.
Colotta et al., Arch. Pharm. Pharm. Med. Chem. 332(2) 39-41, 1999 4-Amino-6-benzylamino-1,2-dihydro-2-phenyl-1,2,4-triazolo [4,3-alpha]-quinoxalin-1-one: a new $A_{2A}$ adenosine receptor antagonist with high selectivity versus $A_1$ receptors.
Auchampach, et al., American Journal of Physiology 276(3 Pt 2) H1113-H1116, 1999, Adenosine receptor subtypes in the heart: therapeutic opportunities and challenges.
Haas et al., Naunyn Schmiedeberg's Archives of Pharmacology 362(4-5) 375-381, 2000, Functions of neuronal adenosine receptors.
Dionisotti et al., British Journal of Pharmacology 121(3) 353-360, 1997 Characterization of human $A_{2A}$ adenosine receptors with the antagonist radioligand [$^3$H]-SCH 58261.
Boutagy et al., Chemical Reviews 74(1) 87-99, 1974 Olefin synthesis with organic phosphonate carbanions.

* cited by examiner

*Primary Examiner*—Rei-tsang Shiao
(74) *Attorney, Agent, or Firm*—George W. Johnston; Patricia S. Rocha-Tramaloni; Kimberly J. Prior

(57) ABSTRACT

The present invention relates to compounds of the general formula

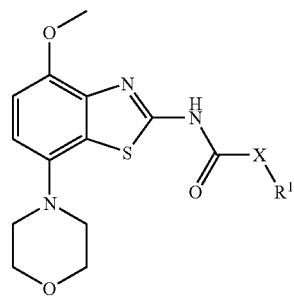

I wherein
$R^1$ is cycloalkyl, substituted by OR or is 2-(7-oxa-bicyclo[2.2.1]hept-1-yl)-ethyl;
R is hydrogen, lower alkyl or C(O)-lower alkyl;
X is —CHR'—; and
R' is hydrogen or lower alkyl;
and pharmaceutically acceptable acid addition salts, optically pure enantiomeres, racemates or diastereomeric mixtures thereof for the treatment of Alzheimer's disease, Parkinson's disease, Huntington's disease, neuroprotection, schizophrenia, anxiety, pain, respiration deficits, depression, ADHD, drug addiction, such as amphetamine, cocaine, opioids, ethanol, nicotine, cannabinoids, or for the treatment of asthma, allergic responses, hypoxia, ischaemia, seizure and substance abuse, or for use as sedatives, muscle relaxants, antipsychotics, antiepileptics, anticonvulsants and cardioprotective agents for coronary artery disease and heart failure.

10 Claims, No Drawings

BENZATHIAZOL-ACETAMIDES

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The action of both subtypes is to increase the amount of available oxygen to tissue and to protect cells against damage caused by a short-term imbalance of oxygen. One of the important functions of endogenous adenosine is preventing damage during traumas such as hypoxia, ischemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho) physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction An increase in neurotransmitter release follows traumas such as hypoxia, ischemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_{2a}$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricular arrhythmias.

Adenosine modulates many aspects of renal function, including renin release, glomerular filtration rate and renal blood flow. Compounds which antagonize the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors, for example the following publications:
Bioorganic &Medicinal Chemistry, 6, (1998), 619-641,
    Bioorganic & Medicinal Chemistry, 6, (1998), 707-719,
    J. Med. Chem., (1998), 41, 2835-2845,
    J. Med. Chem., (1998), 41, 3186-3201,
    J. Med. Chem., (1998), 41, 2126-2133,
    J. Med. Chem., (1999), 42, 706-721,
    J. Med. Chem., (1996), 39, 1164-1171,
    Arch. Pharm. Med. Chem., 332, 39-41, (1999), Am. J. Physiol., 276, H1113-1116, (1999) or
Naunyn Schmied, Arch. Pharmacol. 362, 375-381, (2000).

SUMMARY OF THE INVENTION

The present invention provides compounds of formula I and pharmaceutically acceptable salts thereof. The present invention also provides methods for the manufacture of such compounds and their pharmaceutically acceptable salts.

In particular the present invention provides compounds of formula I

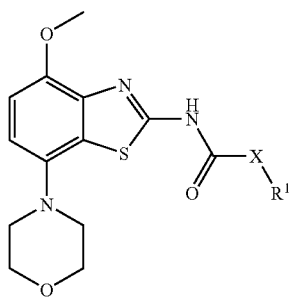

I wherein
R[1] is cycloalkyl substituted by OR or is 2-(7-oxa-bicyclo [2.2.1]hept-1-yl)-ethyl;
R is hydrogen, lower alkyl or C(O)-lower alkyl;
X is —CHR'—; and
R' is hydrogen or lower alkyl;

or a pharmaceutically acceptable acid addition salt, optically pure enantiomer, racemate or diastereomeric mixture thereof.

Compounds of formula I are adenosine receptor ligands. Specifically, the compounds of the present invention have a good affinity to the $A_{2A}$-receptor and a high selectivity to the $A_1$- and $A_3$ receptors. Therefore, the compounds are useful for the treatment of diseases related to the adenosine $A_2$ receptor.

The present invention provides pharmaceutical compositions containing compounds of formula I and a pharmaceutically acceptable carrier. The invention further provides methods for the treatment of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or for the treatment of asthma, allergic responses, hypoxia, ischemia, seizure and substance abuse. Furthermore, compounds of the present invention may be useful as sedatives, muscle relaxants, antipsychotics, antiepileptics, anticonvulsants and cardioprotective agents for disorders such as coronary artery disease and heart failure. The most preferred indications in accordance with the present invention are those, which base on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "cycloalkyl" denotes a saturated carbocyclic group, containing 3-7 carbon atoms.

The term "pharmaceutically acceptable" such as pharmaceutically acceptable carrier, excipient, salts, etc., means pharmacologically acceptable, generally safe, substantially non-toxic to the subject to which the particular compound is administered, and neither biologically nor otherwise undesirable.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" means an amount that is effective to prevent, alleviate or ameliorate symptoms of disease or prolong the survival of the subject being treated.

The present invention provides compounds of formula I

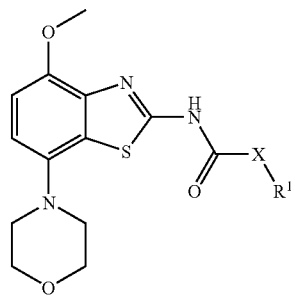

I wherein
R[1] is cycloalkyl substituted by OR or is 2-(7-oxa-bicyclo [2.2.1]hept-1-yl)-ethyl;
R is hydrogen, lower alkyl or C(O)-lower alkyl;
X is —CHR'—; and
R' is hydrogen or lower alkyl;

or a pharmaceutically acceptable acid addition salt, optically pure enantiomer, racemate or diastereomeric mixture thereof.

In one embodiment, the invention provides compounds of formula I in which X is —CH$_2$—.

Preferred compounds of the present application are compounds of formula I, wherein R[1] is substituted cyclopentyl and X is —CH$_2$—, for example
(cis)-2-(3-acetoxy-cyclopentyl)-N-(4-methoxy-7-morpholin-4-yl-benzothiazol-2-yl)-acetamide,
(cis)-2-(3-acetoxy-cyclopentyl)-N-(4-methoxy-7-morpholin-4-yl-benzothiazol-2-yl)-acetamide,
(−)-(cis)-2-(3-hydroxy-cyclopentyl)-N-(4-methoxy-7-morpholin-4-yl-benzothiazol-2-yl)-acetamide and
(+)-(cis)-2-(3-hydroxy-cyclopentyl)-N-(4-methoxy-7-morpholin-4-yl-benzothiazol-2-yl)-acetamide.

Further preferred are compounds, wherein $R^1$ is substituted cyclohexyl and X is —$CH_2$—, for example
(cis)-2-(4-hydroxy-cydohexyl)-N-(4-methoxy-7-morpholin-4-yl-benzothiazol-2-yl)-acetamide and
(trans)-2-(4-hydroxy-cydohexyl)-N-(4-methoxy-7-morpholin-4-yl-benzothiazol-2-yl)-acetamide.

In another embodiment, the invention provides compounds of formula I in which X is CH-lower alkyl.

A further preferred embodiment of the invention are those compounds, wherein $R^1$ is 2-(7-oxa-bicyclo [2.2.1]hept-1-yl)-ethyl, for example
(rac)-N-(4-methoxy-7-morpholin-4-yl-benzothiazol-2-yl)-2-(7-oxa-bicyclo [2.2.1]hept-1-yl)-propionamide.

The present compounds of formula I and their pharmaceutically acceptable salts can be prepared by methods known in the art, for example, by processes described below, which process comprises
reacting a compound of formula

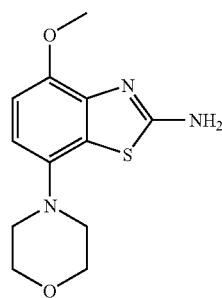

II with a compound of formula

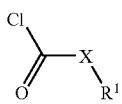

III to produce a compound of formula

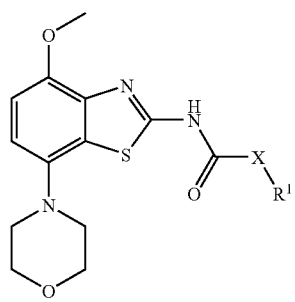

I wherein $R^1$ and X have the significances given above, and
if desired, converting the compounds obtained into pharmaceutically acceptable acid addition salts.

In Examples 1-7 the preparation of compounds of formula I is described in more detail.

The starting materials are known compounds or can be prepared according to methods known in the art.

Preparation of Compounds of Formula I

The intermediate 7-(morpholin-4-yl)-4-methoxy-benzothiazol-2-ylamine can be prepared according to methods disclosed in WO01/97786. The preparation of compounds of formula (I) using the intermediate of formula (II) is also described in WO01/97786.

For example a compound of formula I can be prepared as follows:

To a solution of a substituted cycloalkaneacetic acid and N,N-dimethylformamide in dichloromethane is added oxalyl chloride and the resulting solution is stirred for about 18 h at ambient temperature. After evaporation of the volatile components in vacuo, the residue is taken up in toluene and again evaporated to dryness. The obtained acid chloride of formula (III) is then dissolved in dichloromethane and subsequently treated with N-ethyl-diisopropyl amine and 4-methoxy-7-morpholin-4-yl-benzothiazol-2-ylamine (II). After stirring for about 2 h at ambient temperature, the mixture is cooled to room temperature and treated with saturated aqueous sodium hydrogen carbonate, extracted and dried. Separation by preparative chiral HPLC affords the desired compound of formula I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I can be basic, for example in cases where the residue R contains a basic group such as an aliphatic or aromatic amine moiety. In such cases the compounds of formula I can be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 μg of membrane protein, 0.5 mg of Ysi-poly-1-lysine SPA beads and 0.1 U adenosine deaminase in a final volume of 200 μl of buffer A. Nonspecific binding was defined using xanthine amine congener (XAC; 2 μM). Compounds were tested at 10 concentrations from 10 μM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The pKi values of compounds of the present application are in the range of 7.7 to 8.5. The preferred compounds show a pKi>8.0.

| Example No. | $hA_2$ (pKi) |
|---|---|
| 1 | 8.0 |
| 2 | 8.2 |
| 3 | 8.2 |
| 4 | 8.2 |
| 5 | 8.2 |
| 6 | 8.5 |
| 7 | 7.7 |

The present invention also provides pharmaceutical compositions containing one or more compound of the invention, or pharmaceutically acceptable salt thereof, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, cornstarch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid of liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

In accordance with the invention compounds of formula I as well as their pharmaceutically acceptable salts are useful in the treatment or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischemia, seizure and substance abuse. Furthermore, compounds of the present invention may be useful as sedatives, muscle relaxants, antipsychotics, antiepileptics, anticonvulsants and cardioprotective agents and for the production of corresponding medicaments.

The most preferred indications in accordance with the present invention are those, which include disorders of the central nervous system, for example the treatment or prevention of Parkinson's disease, neuroprotection or certain depressive disorders.

Thus, the present invention provides a method for treating central nervous system disorders mediated by $A_{2A}$ which comprises administering to an individual a therapeutically effective amount of a compound of formula I. In particular, the present invention provides a method of treating Parkinson's disease which comprises administering to an individual a therapeutically effective amount of a compound of formula I. The invention also provides a method of treating depression which comprises administering to an individual a therapeutically effective amount of a compound of formula I. The invention further provides a method of neuroprotection which comprises administering to an individual a therapeutically effective amount of a compound of formula I.

The compounds and compositions of the invention can be administered in a conventional manner, for example, orally, rectally, or parenterally. The compounds and compositions of the invention can be administered orally, for example, in the form of tablets, coated tablets, dragées, hard and soft gelatine capsules, solutions, emulsions, or suspensions. The compounds and compositions of the invention also can be administered rectally, for example, in the form of suppositories, or parenterally, for example, in the form of injectable solutions.

The dosage at which the compounds can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as a single dose or in divided doses and, in addition, the upper limit can also be exceeded when indicated.

| | Tablet Formulation (Wet Granulation) | | | | |
|---|---|---|---|---|---|
| | | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

(cis)-2-(3-Acetoxy-cyclopentyl)-N-(4-methoxy-7-morpholin-4-yl-benzothiazol-2-yl)-acetamide To a solution of (rac)-(cis)-3-(acetyloxy)-cyclopentaneacetic acid (770 mg, 4.1 mmol) and N,N-dimethylformamide (0.01 ml, 0.13 mmol) in dichloromethane (10 ml) were added oxalyl chloride (1.4 ml, 17 mmol) and the resulting solution stirred for 18 h at ambient temperature. After evaporation of the volatile components in vacuo, the residue was taken up in toluene (10 ml) and again evaporated to dryness. The obtained acid chloride was then dissolved in dichloromethane (20 ml) and subsequently treated with N-ethyldiisopropyl amine (2.5 ml, 15 mmol) and 4-methoxy-7-morpholin-4-yl-benzothiazol-2-ylamine (960 mg, 3.6 mmol). After stirring for 2 h at ambient temperature and another hour at 50° C., the mixture was cooled to room temperature and treated with saturated aqueous sodium hydrogen carbonate (15 ml) and extracted twice with dichloromethane (20 ml each). After drying over magnesium sulphate and evaporation of the solvents, flash chromatography (silica, eluent dichloromethane/ethyl acetate 85:15) afforded (rac)-(cis)-2-(3-acetoxy-cyclopentyl)-N-(4-methoxy-7-morpholin-4-yl-benzothiazol-2-yl)-acetamide as off-white solid. Separation by preparative chiral HPLC (Chiralpack AD, eluent heptane/isopropanol 85:15) afforded the title compound as first eluting isomer. Light yellow solid (4% yield). MS: m/e=434(M+H$^+$), mp 171-172° C.

Following the general method of example 1 the compounds of examples 2 to 7 were prepared.

EXAMPLE 2

(cis)-2-(3-Acetoxy-cyclopentyl)-N-(4-methoxy-7-morpholin-4-yl-benzothiazol-2-yl)-acetamide Using 4-methoxy-7-morpholin-4-yl-benzothiazol-2-ylamine and (rac)-(cis)-acetic acid 3-chlorocarbonylmethyl-cyclopentyl ester, (rac)-(cis)-2-(3-acetoxy-cyclopentyl)-N-(4-methoxy-7-morpholin-4-yl-benzothiazol-2-yl)-acetamide was obtained. Separation by preparative chiral HPLC (Chiralpack AD, eluent heptane/isopropanol 85:15) afforded the tide compound as later eluting isomer. Light yellow crystals (4% yield). MS: m/e=434(M+H$^+$), mp 172-173° C.

EXAMPLE 3

(−)-(cis)-2-(3-Hydroxy-cyclopentyl)-N-(4-methoxy-7-morpholin-4-yl-benzothiazol-2-yl)-acetamide (cis)-2-(3-Acetoxy-cyclopentyl)-N-(4-methoxy-7-morpholin-4-yl-benzothiazol-2-yl)-acetamide (first eluting isomer, 64 mg, 0.15 mmol), potassium carbonate (82 mg, 0.59 mmol) and sodium methoxide (5.4M in methanol, 1.37 ul, 0.0074 mmol) are stirred together in methanol (6 ml) for 4 h at ambient temperature. Evaporation of the solvent, dissolution in methylene chloride and extraction with saturated sodium carbonate afforded, after drying and evaporation of the methylene chloride, a crude material. After crystallization from diethyl ether, the title compound was obtained as light yellow crystals (91% yield). MS: m/e=392(M+H$^+$), mp 168-171° C., $\alpha_{589}$=−4.87 (CH$_2$Cl$_2$, c=1.1%).

EXAMPLE 4

(+)-(cis)-2-(3-Hydroxy-cyclopentyl)-N-(4-methoxy-7-morpholin-4-yl-benzothiazol-2-yl)-acetamide (cis)-2-(3-Acetoxy-cyclopentyl)-N-(4-methoxy-7-morpholin-4-yl-benzothiazol-2-yl)-acetamide (later eluting isomer, 64 mg, 0.15 mmol), potassium carbonate (82 mg, 0.59 mmol) and sodium methoxide (5.4M in methanol, 1.37 ul, 0.0074 mmol) are stirred together in methanol (6 ml) for 4 h at ambient temperature. Evaporation of the solvent, dissolution in methylene chloride and extraction with saturated sodium carbonate afforded, after drying and evaporation of the methylene chloride, a crude material. After crystallization from diethyl ether, the title compound was obtained as light yellow crystals (90% yield). MS: m/e=392(M+H$^+$), mp 167-170° C., $\alpha_{589}$=+4.32 (CH$_2$Cl$_2$, c=1.1%).

EXAMPLE 5

(cis)-2-(4-Hydroxy-cyclohexyl)-N-(4-methoxy-7-morpholin-4-yl-benzothiazol-2-yl)-acetamide Using 4-methoxy-7-morpholin-4-yl-benzothiazol-2-ylamine and (cis)-acetic acid 4-chlorocarbonylmethyl-cyclohexyl ester, the tide compound was synthesized in exact the same manner as (cis)-2-(3-acetoxy-cyclopentyl)-N-(4-methoxy-7-morpholin-4-yl-benzothiazol-2-yl)-acetamide and obtained as light yellow crystals (33% yield). MS: m/e=406 (M+H$^+$), mp 212-216° C.

EXAMPLE 6

(trans)-2-(4-Hydroxy-cyclohexyl)-N-(4-methoxy-7-morpholin-4-yl-benzothiazol-2-yl)-acetamide Using 4-methoxy-7-morpholin-4-yl-benzothiazol-2-ylamine and (trans)-acetic acid 4-chlorocarbonylmethyl-cyclohexyl ester, the title compound was synthesized in exact the same manner as described for (cis)-2-(4-Hydroxy-cyclohexyl)-N-(4-methoxy-7-morpholin-4-yl-benzothiazol-2-yl)- acetamide and obtained as light yellow crystals (51% yield). MS: m/e=406(M+H⁺), mp 190-192° C.

EXAMPLE 7

(rac)-N-(4-Methoxy-7-morpholin-4-yl-benzothiazol-2-yl)-2-(7-oxa-bicyclo[2.2.1]hept-1-yl)-propionamide Using 4-methoxy-7-morpholin-4-yl-benzothiazol-2-ylamine and 2-(7-oxa-bicyclo[2.2.1]hept-1-yl)-propionyl chloride, the title compound was obtained as white solid (67% yield). MS: m/e=418(M+H⁺), mp 195-197° C.

EXAMPLE 8

Intermediate (rac)-2-(7-Oxa-bicyclo [2.2.1]hept-1-yl)-propionic acid

The title compound was prepared by standard Wittig-Horner reaction from 4-hydroxy-cyclohexanone, 2-(diethoxy-phosphoryl)-propionic acid ethyl ester and sodium hydride (J. Boutagy, R. Thomas, *Chem. Rev.* 1974, 74, 87-99) and subsequent saponification with potassium hydroxide in ethanol. After recrystallization from n-heptane, the title compound was obtained as white solid. EI-MS: m/e=170(M⁺), ¹H-NMR (90 MHz, CDCl₃, TMS): δ 1.3 (d, J=8 Hz, 3H, Me), 1.7 (m, 8H, CH₂), 3.0 (q, J=8 Hz, 1H, CH-Me), 4.6 (t, J=4.5 Hz, 1H, CH—O), 7.2 (s, 1H, COOH), mp 61-62° C., bp 120° C. (0.008 mbar).

The invention claimed is:
1. A compound of formula I

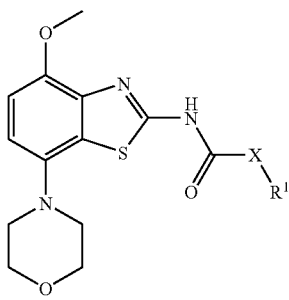

wherein
R¹ is cycloalkyl substituted by OR or is 2-(7-oxa-bicyclo[2.2.1]hept-1-yl)-ethyl;
R is hydrogen, lower alkyl or C(O)-lower alkyl;
X is —CHR'—; and
R' is hydrogen or lower alkyl;
or a pharmaceutically acceptable acid addition salt, optically pure enantiomer, racemate or diastereomeric mixture thereof:

2. A compound of formula I according to claim 1, wherein X is —CH₂—.
3. A compound of formula I according to claim 2, wherein R¹ is substituted cyclopentyl.
4. A compound of formula I according to claim 3, selected from the group consisting of
(cis)-2-(3-acetoxy-cyclopentyl)-N-(4-methoxy-7-morpholin-4-yl-benzothiazol-2-yl)-acetamide,
(cis)-2-(3-acetoxy-cyclopentyl)-N-(4-methoxy-7-morpholin-4-yl-benzothiazol-2-yl)-acetamide,
(−)-(cis)-2-(3-hydroxy-cyclopentyl)-N-(4-methoxy-7-morpholin-4-yl-benzothiazol-2-yl)-acetamide, and
(+)-(cis)-2-(3-hydroxy-cyclopentyl)-N-(4-methoxy-7-morpholin-4-yl-benzothiazol-2-yl)-acetamide.
5. A compound of formula I according to claim 2, wherein R¹ is substituted cyclohexyl.
6. A compound of formula I according to claim 5, selected from the group consisting of
(cis)-2-(4-hydroxy-cyclohexyl)-N-(4-methoxy-7-morpholin-4-yl-benzothiazol-2-yl)-acetamide and
(trans)-2-(4-hydroxy-cyclohexyl)-N-(4-methoxy-7-morpholin-4-yl-benzothiazol-2-yl)-acetamide.
7. A compound of formula I according to claim 1, wherein X is CH-lower alkyl.
8. A compound of formula I according to claim 1, wherein R¹ is 2-(7-oxa-bicyclo[2.2.1]hept-1-yl)-ethyl.
9. A compound of formula I according to claim 8, wherein the compound is
(rac)-N-(4-methoxy-7-morpholin-4-yl-benzothiazol-2-yl)-2-(7-oxa-bicyclo[2.2.1]hept-1-yl)-propionamide.
10. A pharmaceutical composition comprising a compound of formula I

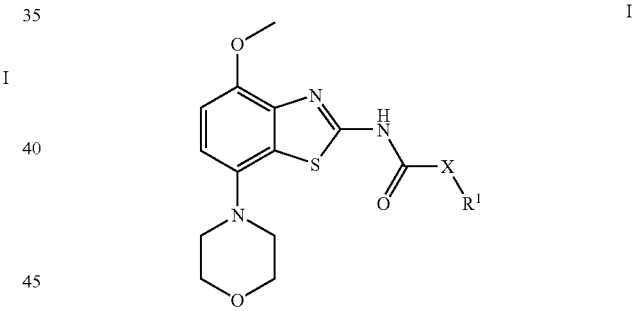

wherein
R¹ is cycloalkyl substituted by OR or is 2-(7-oxa-bicyclo[2.2.1]hept-1-yl)-ethyl;
R is hydrogen, lower alkyl or C(O)-lower alkyl;
X is —CHR'—; and
R' is hydrogen or lower alkyl;
or a pharmaceutically acceptable acid addition salt, optically pure enantiomer, racemate or diastereomeric mixture thereof and a pharmaceutically acceptable carrier.

* * * * *